United States Patent [19]

Uchiyama et al.

[11] Patent Number: 5,909,114
[45] Date of Patent: Jun. 1, 1999

[54] COULOMETRIC ANALYSIS METHOD AND A DEVICE THEREFOR

[75] Inventors: Shunichi Uchiyama, Fukaya; Takeshi Sato, Toki; Hirofumi Akano, Handa; Yoshiya Kawamura, Konan, all of Japan

[73] Assignee: Nakano Vinegar Co., Ltd., Handa, Japan

[21] Appl. No.: 08/957,393

[22] Filed: Oct. 23, 1997

Related U.S. Application Data

[63] Continuation of application No. 08/745,518, Nov. 12, 1996, abandoned, which is a continuation of application No. 08/145,445, Oct. 28, 1993, abandoned.

[30] Foreign Application Priority Data

Oct. 28, 1992 [JP] Japan .................................. 4-290156
Feb. 19, 1993 [JP] Japan .................................. 5-030928
Jul. 1, 1993 [JP] Japan .................................. 5-163606
Sep. 7, 1993 [JP] Japan .................................. 5-222527

[51] Int. Cl.$^6$ .................................................. G01N 27/26
[52] U.S. Cl. ........................... 324/94; 204/415; 324/425
[58] Field of Search ................................ 324/92, 93, 94, 324/425, 439, 440, 441; 204/406, 407, 415; 205/782.5, 792, 793; 422/82.01; 435/26; 436/149, 151

[56] References Cited

U.S. PATENT DOCUMENTS 3,621,381 11/1971 Eckfeldt .................................. 324/441
3,657,647 4/1972 Beusman et al. ....................... 324/94
4,005,002 1/1977 Racine et al. .......................... 204/415
4,029,563 6/1977 Binder et al. .......................... 204/432
4,225,410 9/1980 Pace ...................................... 204/407

(List continued on next page.)

FOREIGN PATENT DOCUMENTS 61-156142 7/1986 Japan .

OTHER PUBLICATIONS

Buchert, J., 1991, "A xylose–oxidizing membrane–bound aldose dehydrogenase of *Gluconobacter oxydans* ATCC 621," J. of Biotechnology, 18:103–113.
Ameyama, et al., 1982, "Aldehyde Dehydrogenase from Acetic Acid Bacteria, Membrane–Bound," Methods in Enzymology, 89:491–497.
Ameyama, et al., 1985, "Solubilization, Purification and Properties of Membrane–bound Glycerol Dehydrogenase from *Gluconobacter industrius*," Agric. Biol. Chem., 49(4):1001–1010.
Shinagawa, et al., 1982, "D–Sorbitol Dehydrogenase from *Gluconobacter suboxydans*, Membrane–Bound," Methods in Enzymology, 89:141–145.
Davidson, V., 1993, "Methylamine Dehydrogenase," Principles and Applications of Quinoproteins, Chpt. 5:73–95.
Barrett, et al., 1984, "Acetaldehyde formation by mitochondria from the free–living nematode *Panagrellus redivivus*," J. Biochem., 221:535–540.

(List continued on next page.)

*Primary Examiner*—Ernest F. Karlsen
*Attorney, Agent, or Firm*—Pennie & Edmonds LLP

[57] ABSTRACT

The present invention provides a rapid coulometric analysis for the quantitative determination of a sample substance with high reproducibility without any application of voltage etc. from the outside, as well as a galvanic cell and a device for use in said coulometric analysis. According to the present invention, a wide variety of components can be analyzed by selection of electroactive substance introduced into the galvanic cell. The present invention enables a simple and easy analysis for food components such as glutamic acid, ascorbic acid, etc., water quality such as COD, etc.

28 Claims, 5 Drawing Sheets

Sectional drawing of galvanic cell 1

U.S. PATENT DOCUMENTS

| | | | |
|---|---|---|---|
| 4,374,186 | 2/1983 | McCartney et al. | 429/154 |
| 4,400,242 | 8/1983 | Albery et al. | 204/415 |
| 4,738,765 | 4/1988 | Cortina et al. | 204/415 |
| 4,839,020 | 6/1989 | Yamaguchi et al. | 204/415 |
| 4,867,860 | 9/1989 | Siddiqi et al. | 204/418 |
| 4,929,313 | 5/1990 | Wrighton | 205/782.5 |
| 4,938,860 | 7/1990 | Wogoman | 204/415 |
| 5,059,290 | 10/1991 | Uchiyama et al. | 204/153.1 |
| 5,133,856 | 7/1992 | Yamaguchi et al. | 204/415 |
| 5,183,712 | 2/1993 | Beldock et al. | 429/9 |
| 5,393,391 | 2/1995 | Dietze et al. | 205/793 |
| 5,443,701 | 8/1995 | Willner et al. | 204/415 |
| 5,720,862 | 2/1998 | Hamamoto et al. | 204/415 |

OTHER PUBLICATIONS

Ameyama, et al., 1981, "D–Fructose Dehydrogenase of *Gluconobacter industrius*: Purification, Characterization, and Application to Enzymatic Microdetermination of D–Frutcose," J. Bacteriology, 145:814–823.

Matsushita, et al., 1989, "Reactivity with Ubiquinone of Quinoprotein D–Clucose Dehydrogenase from *Gluconobacter suboxydans*," J. Biochem., 105:633–637.

Shuppan, 1990, "Annotation in the hygienic test method," Pharma. Soc. of Japan, pp. 310–313 (translation provided).

Van Der Schoot, et al., "Coulometric Sensors, The Application of a Sensor–Actuator System for Long–Term Stability in Chemical Sensing," Sensors & Actuators, vol. 13, No. 3, (1988) 251–262.

FIG. 1

Sectional drawing of galvanic cell 1

COULOMETRIC ANALYSIS METHOD AND A DEVICE THEREFOR

This is a continuation, of application Ser. No. 08/745,518, filed Nov. 12, 1996, now abandoned, which is a continuation of Ser. No. 08/145,445, filed Oct. 28, 1993, now abandoned.

FIELD OF THE INVENTION

The present invention relates to a coulometric analysis method (self-driven coulometry) for the quantitative determination of a sample substance by cell reaction, as well as a galvanic cell and a device used for said method.

BACKGROUND OF THE INVENTION

For the quantitative determination of a sample substance, conventional electroanalysis using electrolysis involves measuring electrical changes occurring in a reaction (e.g., oxidation, reduction, etc.) of the substance under application of constant voltage or current, and in recent years, electrically conductive porous electrodes have been applied to such analysis.

Conventional electroanalysis using ion electrodes is a method in which an ion passing through a separating membrane is detected and in which an equilibrium potential between ions resulting from a sample substance and an electrode membrane is electrically measured by each electrode immersed as a detector in a sample solution. Another conventional electroanalysis using conductive porous electrodes is a method in which a sample is directly electrolyzed in a detection chamber with a conductive porous substance impregnated with an electrolyte, as described e.g. in Japanese Published Unexamined Patent Application 195,358/89. According to this patent application, however, electrical energy should be supplied from the outside, and a long time is required for the stabilization of the measurement device.

Conventional analysis by a reaction via a mediator makes use of a reaction e.g. from nicotinamide adenine dinucleotide (NAD) to reduced nicotinamide adenine dinucleotide (NADH) by dehydrogenase. For such a method, a glutamic acid assay kit (manufactured by BMY Co., Ltd.), for example, is commercially available for the quantitative determination in colorimetry of glutamic acid by glutamate dehydrogenase.

However, the aforesaid electroanalysis by ion electrodes have problems such as a long measurement time due to a slow rate of ion transfer through a separating membrane and a slow response rate of reaching equilibrium, etc., and troublesome procedures such as the step of washing required after each measurement, etc.

The above electroanalysis by electrolysis also has a problem. Electrolysis of a sample substance needs constant voltage or current from an external power source. Such application of voltage, however, causes the electrodes to be in a nonequilibrium state where so-called "capacitative current" occurs. Therefore, every time voltage is applied, a long stabilization time is required for measurement by electrolysis. Another problem is that the device should be made complex because of the necessity of constant voltage or current generating units, etc.

Furthermore, the above-mentioned measurement by enzyme reaction via a mediator requires the troublesome procedures of forming e.g. NADH with an enzyme, then reacting it with diaphorase etc., and measuring its absorbance. There are also practical problems: e.g., a refrigerator is required for storage of enzyme etc., and a sensor intended for use at room temperature cannot used for enzyme. In addition, it is not possible to accurately determine the absorbance where a colored substance is present in the sample.

SUMMARY OF THE INVENTION

The object of the present invention is to solve the above problems in the conventional methods and provide a coulometric analysis method for the quantitative determination of a sample substance by cell reaction, as well as a galvanic cell and a device used for said method, which does not require electrical energy such as voltage, current, etc., from an external power source and enables the rapid determination of a sample substance.

To accomplish the above object, the present inventors have made extensive research and discovered that a potential difference (electro chemical potential difference) occurs between working and counter electrodes in oxidoreduction between a component of working electrode and a sample substance where the electrical quantity generated by the potential difference is closely related to the amount of the sample substance, and that the reaction can proceed spontaneously and rapidly by selecting suitable components for the electrodes.

That is, the present invention relates to a method of coulometric analysis for the quantitative determination of a sample substance, wherein at least one of voltage, current, and electrical quantity occurring between electrodes is measured without any application of voltage from the outside, with a galvanic cell having a working electrode containing a sample substance, a counter electrode containing an electroactive substance, a material being located in an adjoining region of both the electrodes and permitting ions to pass therethrough. By the wording "electroactive substance" is meant a chemical species participating in discharge reaction to give electromotive force as an electrochemical active species.

The present invention further relates to a method for coulometric analysis of glutamic acid, which comprises using said galvanic cell with NADH or a derivative thereof as an indicator.

In addition, the present invention relates to a method for coulometric analysis of chemical oxygen demand (COD), which comprises using potassium permanganate as an indicator and said galvanic cell with the working electrode impregnated with an electrolyte and the counter electrode impregnated with hexacyanoferrate (II) ion as electroactive substance.

Furthermore, the present invention is directed to a method for coulometric analysis of COD, which comprises using potassium permanganate as an indicator and said galvanic cell with the working electrode impregnated with an electrolyte and the counter electrode impregnated with hexacyanoferrate (II) ion and hexacyanoferrate (III) ion as electroactive substance.

Finally, the present invention is concerned with a method for coulometric analysis of ascorbic acid, which comprises using said galvanic cell with the working electrode impregnated with an electrolyte and/or 3,7 bis(dimethylamino) phenothiazine-5-ium chloride and the counter electrode impregnated with hexacyanoferrate (III) ion as electroactive substance.

DETAILED DESCRIPTION OF THE INVENTION

In the present invention, the above galvanic cell comprises the working electrode made of a hydrophilic and conductive material impregnated with an electrolyte (in case the sample is an electroactive substance) or with an electrolyte and/or a mediator (in case the sample reacts electrochemically with a mediator to form an electroactive substance); an upper component provided with a penetrating hole including said working electrode, with the side having an electrode terminal joined to said working electrode; a counter electrode made of a hydrophilic and conductive material impregnated with an electroactive substance; a lower component provided with a concave part receiving said counter electrode, with the side having an electrode terminal joined to said counter electrode and the bottom having a liquid-supplement hole; a lid component for closing said liquid-supplement hole; an ion-permeable separating membrane located between said upper and lower components; and a fixing component being fitted to said penetrating hole in said upper component and being pressed on said working electrode. The conductive material used for said working electrode may be provided on its periphery with a water-absorptive material e.g. a filter paper, so that discharging occurs rapidly owing to rapid dispersion of a solution into the working electrode, and the working electrode can be successively used without being replaced by a new working electrode, owing to absorption of an excess amount of a sample solution into the water-absorptive material.

This galvanic cell is provided with a current integration means, an indication part, an analysis item selection part, a start button for initiation of current integration by said current integration means, and an arithmetic means of converting integrated electrical quantity into a substance amount which is indicated in said indication part. Quantitative analysis can be easily effected by detachably inserting a pair of electrode terminals of the galvanic cell into a pair of terminals of the electroanalyzer. The indication part can indicate flowing current as well as integrated electrical quantity.

The galvanic cell and electroanalyzer of the present invention are preferably used for the analysis of COD using an indicator such as NADH, ascorbic acid or potassium permanganate.

The present method is based on a coulometric analysis for the quantitative determination of a sample substance (i.e., a chemical species which reacts with an electroactive substance or a mediator to form an electroactive substance) comprising measurement of the electrical energy discharging in a short time from cell reaction of said sample substance. Hence, the present method completely differs in the principle from a conventional method for quantitative determination where a sample is electrolyzed with electrical energy from an external power source.

In the present invention, the working electrode is an electrode containing said sample substance, and the working electrode can be impregnated with an electrolyte and/or a mediator. The electrode solution may be any electrolyte, e.g. a solution of hydrochloric acid, sulfuric acid or potassium chloride, or phosphate buffer. The mediator includes e.g. 5-methylphenazinium methyl sulfate (phenazine methosulfate), 1-methoxy-5-methylphenazinium methyl sulfate (methoxyphenazine methosulfate), 9-dimethylamino benzo [α] phenoxazine-7-ium chloride (Meldola blue) or 3,7bis (dimethylamino) phenothiazine-5-ium chloride (methylene blue) and salts thereof.

The counter electrode is an electrode containing an electroactive substance such as hexacyanoferrate (III) ion and/or hexacyanoferrate (II) ion. Such ions can be used in the form of a salt solution which e.g. is potassium hexacyanoferrate (III) and/or potassium hexacyanoferrate (II) dissolved in an electrode solution.

The substance located in an adjoining region of the electrodes and permitting ions to pass therethrough may be any substance which allows ions to pass there through while preventing direct mixing of the substances contained in the electrodes. Examples are an ion-exchange membrane for use as a separating membrane, agar gel containing an electrolyte for use as a salt bridge, etc.

In the present invention, the device does not require any external power source such as voltage-generating unit for applying voltage between the electrodes, and it requires at least one detector of voltmeter, ammeter and current integrator, and their combination is not particularly limited. A conductor with high current collection effect, such as carbon and metal, may be inserted into between the electrodes so that cell reaction can rapidly proceed in the measurement of electrical quantity etc. The carbon may be any commercial one such as carbon felt etc., and the metal may be any metal with high conductivity such as gold, platinum, silver, lead, etc.

The device of the present invention can be used for the quantitative determination of a sample substance on the basis of the electrical energy generated in the reaction of an electroactive substance in the working electrode with an electroactive substance in the counter electrode. In measurement, the device of the present invention receives as cell current the electrical energy generated in reaction of an electroactive substance in the working electrode and an electroactive substance in the counter electrode, and the cell current can then be converted into the amount of the sample substance. A wide variety of components can be analyzed by selection of a suitable electroactive substance introduced into the electrodes.

Each electrochemically active substance (electrochemically active species) in solution form exhibits an electrode potential inherent in the substance itself. The substance producing a potential difference between the electrodes can be electrolyzed by sufficiently impressed electromotive force from an external power source. In this case, an oxidation reaction occurs in one electrode, and a reduction reaction occurs in another electrode. This is the principle of electrolysis where electrical energy is converted into chemical energy.

Generally speaking, an electric potential occurring in electrode oxidation is often higher than an electric potential in electrode reduction, so that electrolysis does not proceed (i.e., coulometric analysis cannot be performed) in the absence of a certain electric potential, e.g. in the form of impressed electromotive force from an external power source.

According to the present invention, however, chemical energy can be converted into electric energy spontaneously and rapidly in the absence of impressed electromotive force from an external power, e.g. by constructing the galvanic cell such that ions can pass through between the counter electrode impregnated with a substance reduced at the electrode at an extremely high potential, such as hexacyanoferrate (III) ion and/or permanganate ion as electroactive substance and the working electrode impregnated with a substance undergoing oxidization by the electrode at an extremely low potential, such as reduced 5-methylphenazinium methyl sulfate, reduced 1-methoxy-5-methylphenazinium methyl sulfate, reduced 9-dimethylaminobenzo [α] phenoxazine-7-ium chloride, reduced 3,7-bis(dimethylamino)phenothiazine-5-ium chloride, hexacyanoferrate (II) ion or ascorbic acid. That is, the sample substance can be quantitatively determined by measurement of the chemical energy possessed by the sample substance as the electrical energy generated by cell reaction.

For example, no reaction occurs between a working electrode containing phenazine methosulfate as a mediator and a counter electrode containing potassium hexacyanoferrate (III) as an electroactive substance because the electroactive substance and the mediator both are in oxidized form. If a reducing substance, such as NADH or a derivative thereof, is added to the working electrode, then the phenazine methosulfate is reduced and oxidation of the resulting phenazine methosulfate occurs at a lower potential than does the reduction of hexacyanoferrate (III) ion in the counter electrode. This generates a potential difference depending on an electrochemical potential between the working and counter electrodes. As a result, cell reaction occurs and this reaction continues until reduced phenazine sulfate is completely oxidized if a sufficient amount of the solution is present in the counter electrode. The current flowing during the cell reaction is measured for the quantitative determination of the reducing agent which has reduced phenazine methosulfate. That is, NADH and its derivative can be quantitatively determined.

The electroactive substance is supplied to the counter electrode through a liquid-supplement hole provided on the bottom of the galvanic cell. The role of a rubber cap provided on the top of the galvanic cell is to prevent drying of the electrodes.

Figure 1:
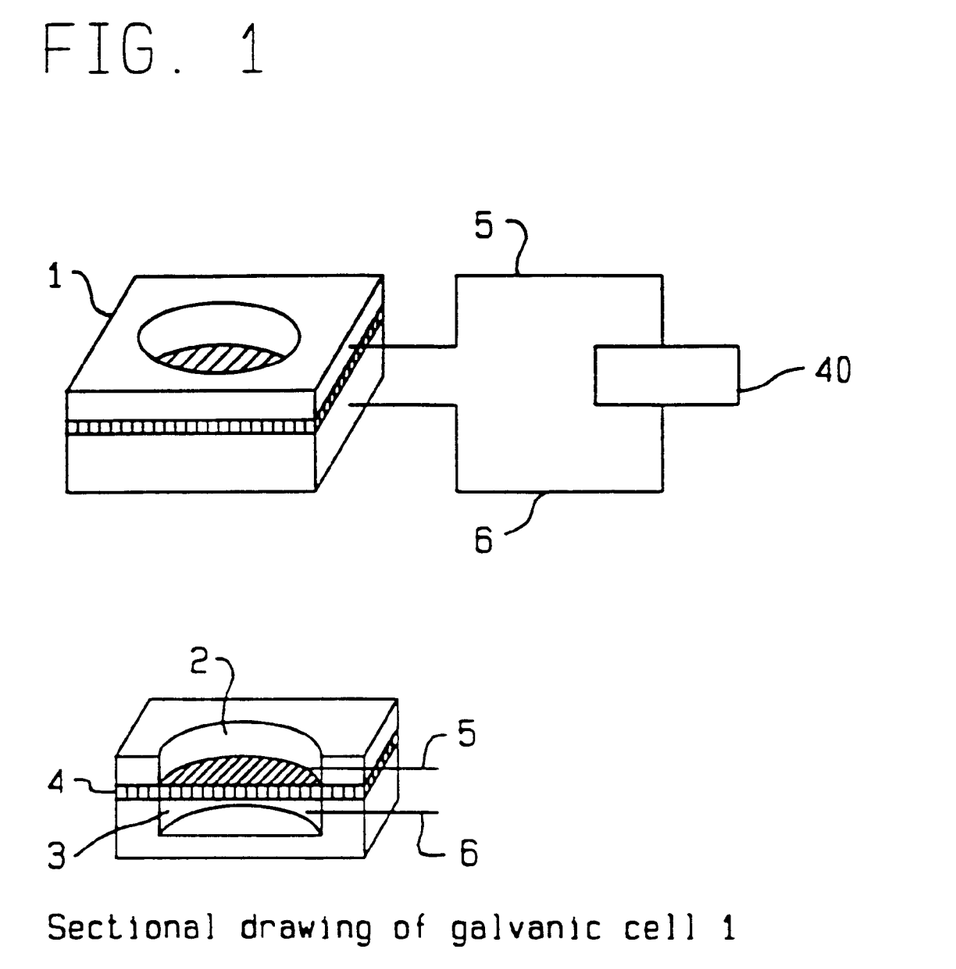
FIG. 1 is a schematic drawing of the device used in the present invention.

FIG. 1 is a schematic drawing of a device used in the present invention. Galvanic cell 1 includes working electrode 2, counter electrode 3, and an ion-exchange membrane serving as separating membrane 4 (cation exchange membrane CMV produced by Asahi Glass Co., Ltd.). The cell is joined via current collection wires 5 and 6 to electroanalyzer 40 (NDCM-1 manufactured by Nichino Keiki Co., Ltd.). Prescribed electrolyte is introduced into the working and counter electrodes 2 and 3, and a certain amount of a sample solution is injected by a syringe into the working electrode 2. The sample can be quantitatively determined by measuring electrical quantity flowing in cell reaction occurring according to the aforementioned principle.

SYMBOL

1: galvanic cell 2: working electrode 3: counter electrode 4: separating membrane 5, 6: current collection electrode wires 7: upper component 8: lower component 9: upper felt 10: lower felt 11,12: packing 13: fixing component 14: cap 15, 16: electrode terminal 17: bottom lid 18,19: sealing hole 20: penetrating hole 21,22: concave parts 23: liquid-supplement hole 25: screw 40: coulometer 42: cutout part 43, 44: terminals 45: electric power switch 46: start button 47: selection button 48: indication part

EXAMPLES

Hereinafter, the present invention is described in more detail with reference to Examples, which however are not intended to limit the scope of the present invention.

Example 1

Selection of Mediator

It was determined with the device in FIG. 1 to what degree the difference of mediator used in measurement of NADH affects the time required for the measurement.

The mediator used in the working electrode was potassium hexacyanoferrate (III), Vitamin $K_3$, methylene blue, phenazine methosulfate (all available from Wako Junyaku Kogyo Co., Ltd.), methoxyphenazine methosulfate (available from Dojin Kagaku Kenkyusho), and Meldola blue (available from Nakarai Tesuku Co., Ltd. ). 3 ml of 0.1M mediator in 0.1M phosphate buffer, pH 7.0, was used as an electrode solution. NADH ($10^{-3}$M) was determined as a sample substance, using the device with the counter electrode containing 0.1M potassium hexacyanoferrate (III) (dissolved in 3 ml of 0.1M phosphate buffer, pH 7.0) as an electrode solution without any application of voltage from an external power source.

As shown in the results in Table 1, the measurements could be effected in a very short time (about 30 seconds) with phenazine methosulfate, methoxyphenazine methosulfate, and Meldola blue as mediator.

TABLE 1

| mediator | measurement time (seconds) |
| --- | --- |
| Vitamin $K_3$ | measurement not possible |
| potassium hexacyanoferrate (III) | 900 |
| methylene blue | 180 |
| phenazine methosulfate | 30 |
| methoxyphenazine methosulfate | 33 |
| Meldola blue | 31 |

Measurement time is a time required until 95% reaction is finished.

Example 2

Measurement of NADH

NADH was measured with the electroanalyzer of Example 10 including the galvanic cell of Example 9.

Figure 2:
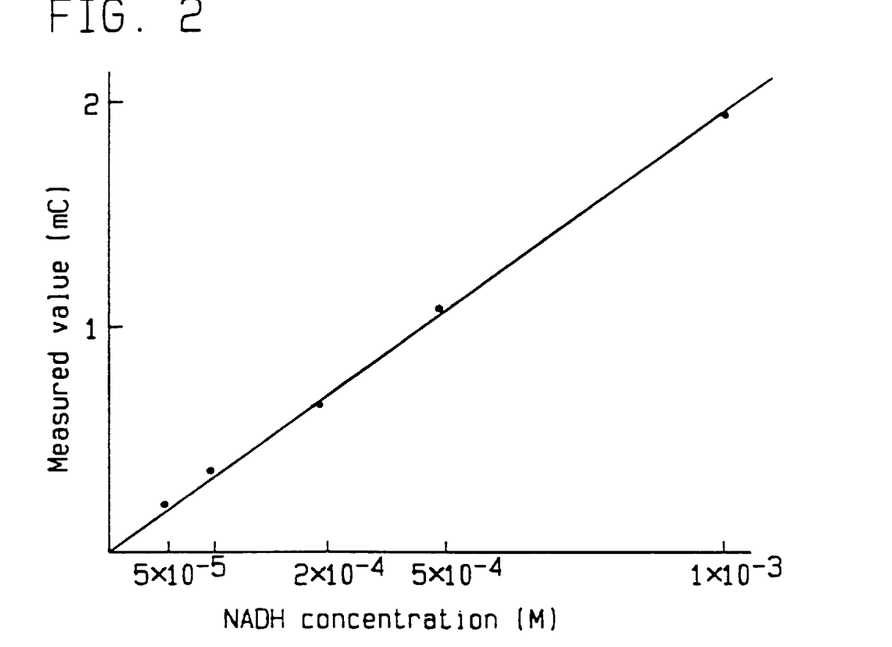
FIG. 2 is a graph showing the relationship between NADH concentration and measured values.

In the galvanic cell, upper felt 9 and lower felt 10 were composed respectively of carbon felts with a top surface area of 7 $cm^2$ thickness of 5 mm, and volume of 3.5 $cm^3$ (GF-20-5F produced by Nippon Carbon Co., Ltd.), and separating membrane 4 was an ion-exchange membrane (cation exchange membrane CMV produced by Asahi Glass Co., Ltd.). For determination of NADH (10 $\mu$l) (dissolved at predetermined concentrations in 40 mM phosphate buffer, pH 7.0), the working electrode was impregnated with 3 ml of 0.1M phenazine methosulfate and the counter electrode with 3 ml of 0.1M potassium hexacyanoferrate (III) (each dissolved in 0.1M phosphate buffer, pH 7.0). As can be seen in FIG. 2, the measurement results obtained in the present coulometric method are in a good linear relationship to the actual concentrations of NADH.

Reproducibility was excellent within 2% coefficient of variation (referred to as "CV", hereinafter) on 10 repeated measurements. When additional measurements were carried out in the same way using the galvanic cell with a carbon felt (GF-20-5F produced by Nippon Carbon Co., Ltd.) inserted into between the working and counter electrodes, the results were also in a good linear relationship to the actual concentrations of NADH. In addition, 10 μl of $5 \times 10^{-4}$M NADH could be measured stably within 2% CV on 200 repeated runs or more.

Example 3
Measurement of glutamic acid by quantitative determination of NADH formed by glutamate dehydrogenase According to the present invention, glutamic acid was quantitatively determined with glutamate dehydrogenase excellent in substrate specificity and stability found by the present inventors (Japanese Patent Application No. 194,245/92). This enzyme catalyzes the following reaction:
L-glutamic acid+$NAD^+$+$H_2O$–α-ketoglutaric acid+NADH+$NH_4^+$ That is, 10 μl of glutamate dehydrogenase (4 U/ml 20 mM phosphate buffer, pH 7.0), as described in Example 1 of Japanese Patent Application No. 194,245/92, was mixed at 30° C. for 3 minutes with 990 μl sodium glutamate solution at a predetermined concentration containing NAD+ (20 mg/ml) as substrate (20 mM phosphate buffer, pH 7.0), and the mixture was measured in the same conditions as in Example 2.

Figure 3:
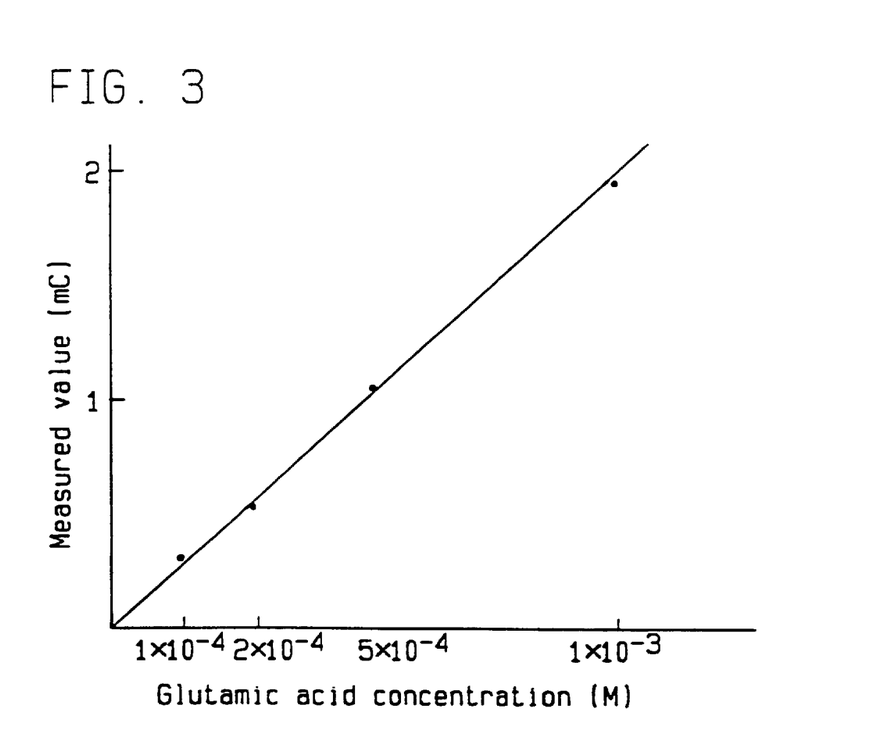
FIG. 3 is a graph showing the relationship between glutamic acid concentrations and measured values.

As shown in the result of FIG. 3, there is a good linear relationship between the values obtained with NADH as an indicator and the actual concentrations of glutamic acid. The glutamic acid content of a sample of commercial soy sauce was determined in the same manner. The content of 11.2 g/l thus determined was in good agreement with the content of 11.3 g/l as determined with an amino acid analyzer (JLC-300 manufactured by Nihon Denshi Co., Ltd.) The content as determined for the same sample by glutamic acid assay kit (manufactured by BMY Co., Ltd.) was 11.0 g/l. In the present invention, the measurements could be effected rapidly, i.e. for about 50 seconds (about 4 minutes even including the enzyme reaction time), whereas the measurements took about 1.5 hours and 20 minutes by the amino acid analyzer and glutamic acid assay kit, respectively.

According to a conventional manner, the enzyme used in this example could be immobilized on the electrode for use.

Example 4
Measurement of glutamic acid by quantitative determination of NADH derivative formed by glutamate dehydrogenase Glutamic acid was determined in the same manner as in Example 3 except that enzyme reaction was carried at 50° C. for 20 minutes in the presence of 3-acetylpyridine NAD (produced by Sigma Co. Ltd.) as coenzyme for glutamate, dehydrogenase (i.e., 3-acetylpyridine NADH formed by enzyme reaction was used as an indicator). The results had a good linear relationship to the real concentrations of glutamic acid. The measurements could be effected in a very short time (about 30 seconds).

Example 5
Chemical oxygen demand (COD) measurement (1)

Various samples were measured for COD using the device of FIG. 1 with the working electrode impregnated with 3 ml of 1N hydrochloric acid containing 0.1M calcium chloride as an electrode solution and the counter electrode impregnated with 3 ml of 1N hydrochloric acid containing 0.01M potassium hexacyanoferrate (II) (ion electroactive substance) and 0.1M potassium chloride as an electrode solution.

Samples were two kinds of waste water from a factory (A and B) and two kinds of treatment sewage (C and D), which all were collected in Handa City, Aichi Prefecture, Japan, as well as 1 mg 0/1 and 10 mg 0/1 glucose standard solutions (described in Japanese Industrial Standards No. JIS K8824).

Measurements were carried out as follows:

2 ml sample, 0.4 ml of 47% sulfuric acid, and 0.2 ml of 0.025N potassium permanganate were introduced in this order into a 10 ml test tube with a cap. The tube was sealed, then heated for 5 minutes and cooled to room temperature. Subsequently, 10 μl of the sample was injected with a syringe into the working electrode of the above device. Separately, the same sample was also measured according to the method as described in Japanese Industrial Standard No. JIS K0102.

As can be seen from the results in Table 2, the measured values according to the present method are in good agreement with those of the JIS K0102 method. In the present method, the measurements could be effected in a short time (about 30 seconds) with a trace amount of sample.

Similar results could be obtained under the same conditions by means of the above device having a carbon felt (GF-20-5F produced by Nippon Carbon Co., Ltd.) inserted into between the working and counter electrodes.

TABLE 2

Result of COD measurement

| sample | present method | JIS K0102 method |
| --- | --- | --- |
| factory waste water A | 8.3 | 7.8 |
| factory waste water B | 8.0 | 7.6 |
| treatment sewage C | 11.0 | 11.5 |
| treatment sewage D | 8.1 | 9.0 |
| glucose standard solutions | | |
| 1 mg 0/1 | 1.1 | 1.2 |
| 10 mg 0/1 | 9.8 | 10.5 | unit: mg 0/1

Example 6
Chemical oxygen demand (COD) measurement (2)

Various samples were measured for COD with the device of FIG. 1 having the working electrode impregnated with 3 ml of 1.5N sulfuric acid as an electrode solution and the counter electrode impregnated with 3 ml of 1.2N sulfuric acid containing 0.02M potassium hexacyanoferrate (II) and 0.02M potassium hexacyanoferrate (III) (ion electroactive substance) as an electrode solution. Samples were two kinds of effluent from septic tanks (A and B) and two kinds of waste water from an office (C and D), which all were collected in Urawa City, Saitama Prefecture, Japan, as well as 1 mg 0/1 and 10 mg 0/1 glucose standard solutions (described in JIS K8824).

Measurements were carried out as follows:

2 ml sample, 0.4 ml of 47% sulfuric acid, and 0.2 ml of 1M silver nitrate, 0.2 ml of 0.025N potassium permanganate were introduced in this order into a 10 ml test tube with a cap. The tube was sealed, then heated for 5 minutes and cooled with water to room temperature. Subsequently, 10 μl of the sample thus treated was injected with a syringe into the working electrode of the above device. Separately, the same sample was also measured according to the method as described in JIS K0102.

As can be seen from the results in Table 3, the measured values according to the present method are in good agreement with those obtained in the JIS K0102 method. In the present method, the measurements could be effected in a short time (about 30 seconds) with a trace amount of sample.

Similar results could be obtained under the same conditions by means of the above device having a carbon felt (GF-20-5F produced by Nippon Carbon Co., Ltd.) inserted into between the working and counter electrodes.

TABLE 3

Result of COD measurement

| sample | present method | JIS K0102 method |
| --- | --- | --- |
| septic tank effluent A | 11.0 | 12.0 |
| septic tank effluent B | 6.7 | 7.4 |
| office waste water C | 23.5 | 24.0 |
| office waste water D | 21.0 | 20.9 |
| glucose standard solutions | | |
| 1 mg 0/1 | 1.1 | 1.2 |
| 10 mg 0/1 | 9.8 | 10.5 | unit: mg 0/1

Example 7

Measurement of ascorbic acid

Ascorbic acid solutions (1–200 mg/100 ml) were measured with the device of FIG. 1 having the working electrode impregnated with 3 ml of 10 mM methylene blue (dissolved in 0.4M phosphate buffer, pH 5.0) and the counter electrode impregnated with 3 ml of 0.4M potassium hexacyanoferrate (III) (0.4M phosphate buffer, pH 7.3) as electrode solution. The ascorbic acid contents thus determined had a good linear relationship to the actual ascorbic acid contents. The measurements could be effected in a short time (about 40 seconds) with a trace sample amount of 5 μl. Stable results were obtained within 2% CV on repeated measurements of the same sample.

Similar results can be obtained with the above device under the same conditions except for the use of 0.4M phosphate buffer, pH 5.0, as an electrode solution in the working electrode, or of a carbon felt (GF-20-5F produced by Nippon Carbon Co., Ltd.) inserted into between the working and counter electrodes.

Example 8

Measurement of ascorbic acid in various commercial foods

The contents of ascorbic acid in various commercial foods were determined using the device of FIG. 1 with the working electrode impregnated with 3 ml of 0.4M phosphate buffer, pH 5.0, as an electrode solution and the counter electrode impregnated with 3 ml of 0.1M potassium hexacyanoferrate (III) (0.4M phosphate buffer, pH 7.3) as an electrode solution. Separately, the same samples were also measured by titration with indophenol and high performance liquid chromatography (HPLC) (published by Shadanhojin Nippon Shokuhin Eisei Kyokai (Japan Food Sanitary Society, Foundation, the 1989 edition, pp. 361–363). Table 4 shows a good agreement among the results.

TABLE 4

Comparion of measured ascorbic acid contents

| sample | indophenol titration method | HPLC method | the present method |
| --- | --- | --- | --- |
| 100% orange juice | 27.6 | 28.9 | 28.6 |
| 10% orange juice | 29.7 | 33.1 | 32.0 |
| non alcoholic beverage | 5.1 | 7.3 | 5.8 |
| cabbage | 29.1 | 33.2 | 28.1 |
| powdered milk | 43.4 | 48.8 | 46.4 | unit: mg/100 mg

Example 9

Figure 4:
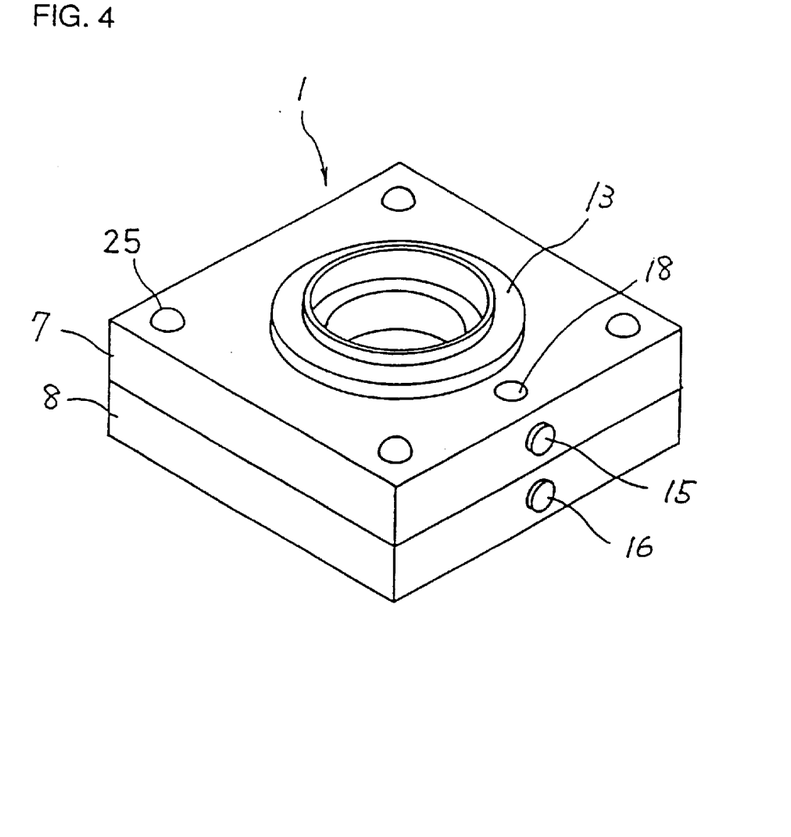
FIG. 4 is a schematic drawing of the galvanic cell in the present examples.
Figure 5:
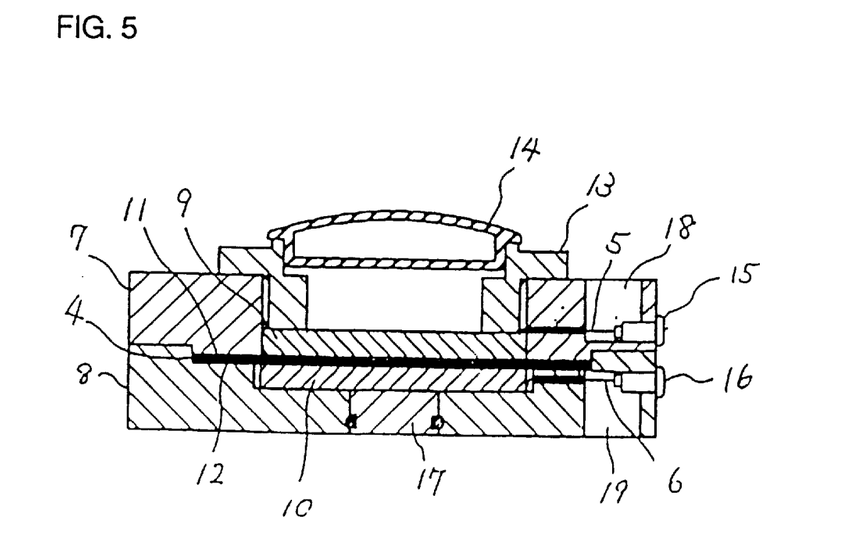
FIG. 5 is a sectional drawing of the galvanic cell shown in FIG. 4.
Figure 6:
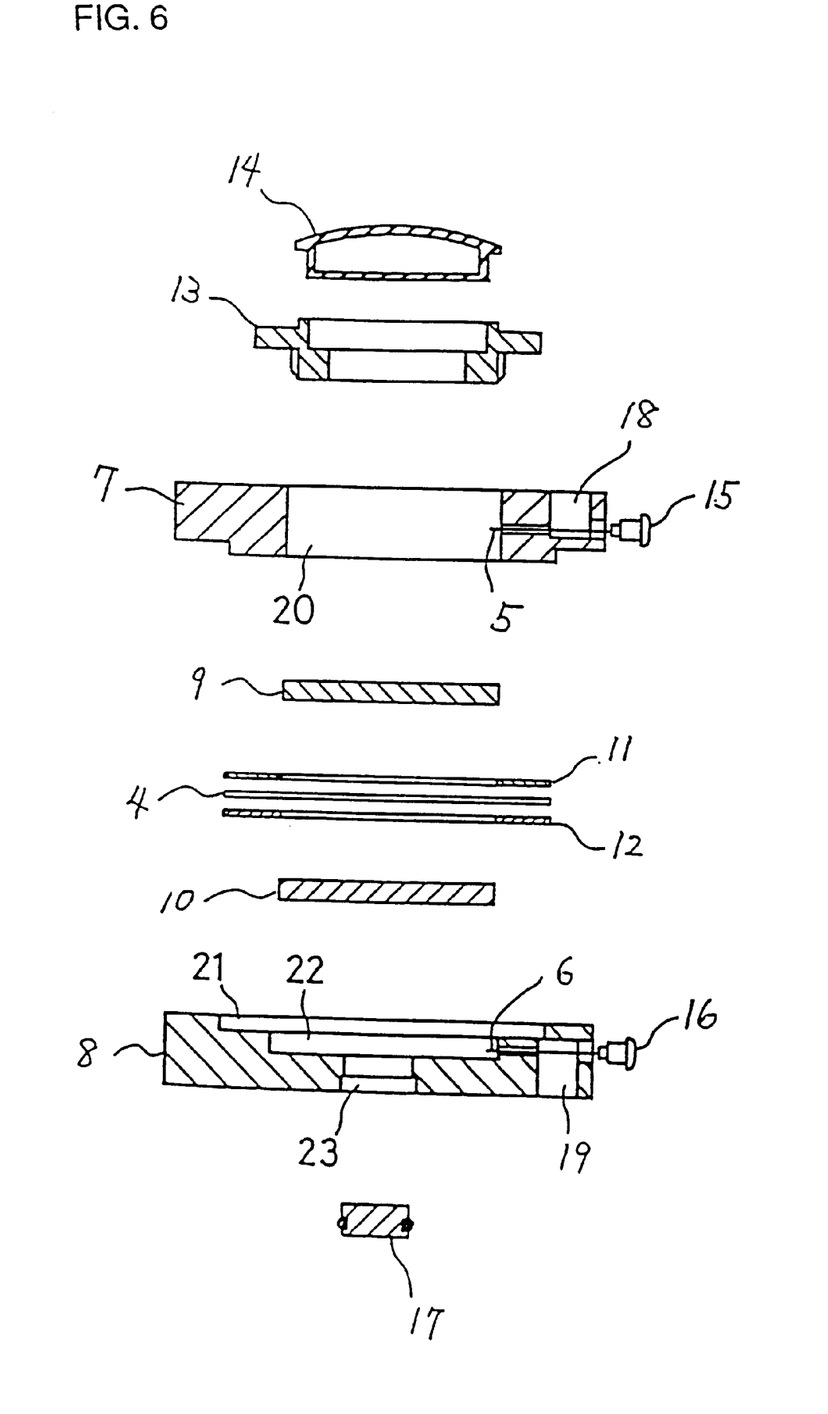
FIG. 6 is a drawing of the structure of the galvanic cell shown in FIG. 4.

The galvanic cell according to the present invention is described by reference to the drawings. FIG. 4 is a drawing of the galvanic cell (without cap 14); FIG. 5 is a sectional drawing; and FIG. 6 is a drawing of the structure of the galvanic cell.

In this example, the galvanic cell includes upper component 7 and lower component 8 each made of an electrical insulating material such as plastics, upper felt 9 and lower felt 10, separating membrane 4, packings 11 and 12 made of a silicone resin etc., collar-head component 13, electrode terminals 15 and 16 to which current collection electrode wires 5 and 6 are connected, bottom lid 17, and cap 14.

The separating membrane 4 is an ion-permeable separating membrane such as glass filter, salt bridge, ion-exchange membrane, etc., among which an ion-exchange membrane such as cation exchange membrane is preferably used for stable measurement.

The upper felt 9 may be any material being hydrophilic and excellent in conductivity such as carbon felt, preferably with a diameter of 30±10 mm or thereabout and thickness of 2–6 mm as will be described below. The lower felt 10 may be any hydrophilic and conductive material, and it preferably has the same size and thickness as the upper felt 9 so that felts 9 and 10 have low electrical resistance, with the same area in contact with the separating membrane 4.

As current collection wires 5 and 6, platinum or gold is used for preventing occurrence of corrosion responsible for a rise in electrical resistance. Electrode terminals 15 and 16 are coated with gold for low electrical resistance so that sufficient conduction is obtainable when the terminals come into contact with the contact points of the measurement device.

The upper component 7, provided vertically with penetrating hole 20, has the bottom with a convex-shaped step fitting the concave part of the lower component. The upper component is also provided horizontally with a thin hole extending from the side to the penetrating hole 20, said thin hole containing the current collection electrode wire 5 joined with solder to the electrode terminal 15. A part of the thin hole crosses the sealing hole 18 extending vertically from the top face to below the thin hole. After insertion of the current collection electrode wire 5 into the thin hole, a resin is introduced into the sealing hole 18 so as to fix the electrode and fill in the thin hole, thus preventing the solution in the electrode cell from leaking out through the thin hole.

The lower component 8 is provided with two concave-shaped steps 21 and 22 on the top surface and with the liquid-supplement hole 23 in the bottom. The lower component is also provided horizontally with a thin hole extending from the side to the concave step 22, said thin hole containing the current collection electrode wire 6 joined with solder to the electrode terminal 16. The lower component 8 is provided with sealing hole 19 in the same manner as in the upper component 7. After insertion of the current collection electrode wire 6 into the thin hole, a resin is introduced into the sealing hole 19 so as to fix the electrode and fill in the thin hole, thus preventing the solution in the electrode cell from leaking out through the thin hole. The bottom lid 17 equipped with an O-ring is attached detachably to the liquid-supplement hole 23.

The galvanic cell is constructed as follows: The lower felt 10 is inserted into the deep concave step 22 of the lower component 8. Then, the round separating membrane 4 with its periphery sandwiched between packings 11 and 12 for preventing mixing anode and cathode solutions is placed on the lower felt 10 such that the packing 12 is located on the hollow concave step 21. The upper component 7 including the upper felt 9 inserted into the penetrating hole 20 is placed on the packing 11 so that the convex-shaped step of the upper felt 7 fits the concave step 21 of the lower component 8. In this state, the upper component 7 is fixed into the lower component 8 with a suitable fixing means such as screw 25 etc. Then, the fixing component 13 is screwed into the penetrating hole 20 of the upper component 7 so as to allow the current collection electrode 5 to be in secure contact with the upper felt 9, while the upper felt 9 is pressed downward so as to come in close contact with the separating membrane 4.

In the galvanic cell according to this embodiment, the upper felt 9 serves as the working electrode, and the lower felt 10 as the counter electrode, and a wide variety of components can be analyzed by selection of a suitable electroactive substance to be introduced into the electrodes. Therefore, a fixing component for the upper felt is used to press the upper felt to secure adhesion between the felt and the separating membrane, thus improving analysis sensitivity. That is, a sample can be quantitatively determined on the basis of the electrical energy generated from an electroactive sample substance or an electroactive substance produced by reaction of an electroactive sample substance with a mediator in one electrode. The role of the electrode terminals of the galvanic cell is to receive current generated by cell reaction. Therefore, the galvanic cell of the present invention does not require any external power supply for application of voltage or current.

Since a sample introduced into the working electrode is converted into a substance inert to cell reaction when analysis is finished, plural samples can successively be analyzed by injection of new sample into the working electrode of the galvanic cell. The electroactive substance consumed by cell reaction is supplied as necessary. With the bottom lid 17 detached, an electroactive substance is supplied through the liquid-supplement hole 23 into the counter electrode. The liquid-supplement hole 23 is preferably 10 mm or more in diameter so that an electroactive substance can be easily introduced.

The role of the rubber cap 14 provided on the top of the galvanic cell is to prevent the electrodes from being dried during analysis or in storage.

The fixing component 13 ensures adhesion between the felt and the separating membrane, thus improving analysis sensibility. For example, if NADH is measured in the absence of the fixing component under the same conditions as in Example 2, the obtained value is lowered (only 60% of theoretical value), and measurements lack accuracy because of poor reproducibility with at least 10% CV.

Example 10

Figure 7:
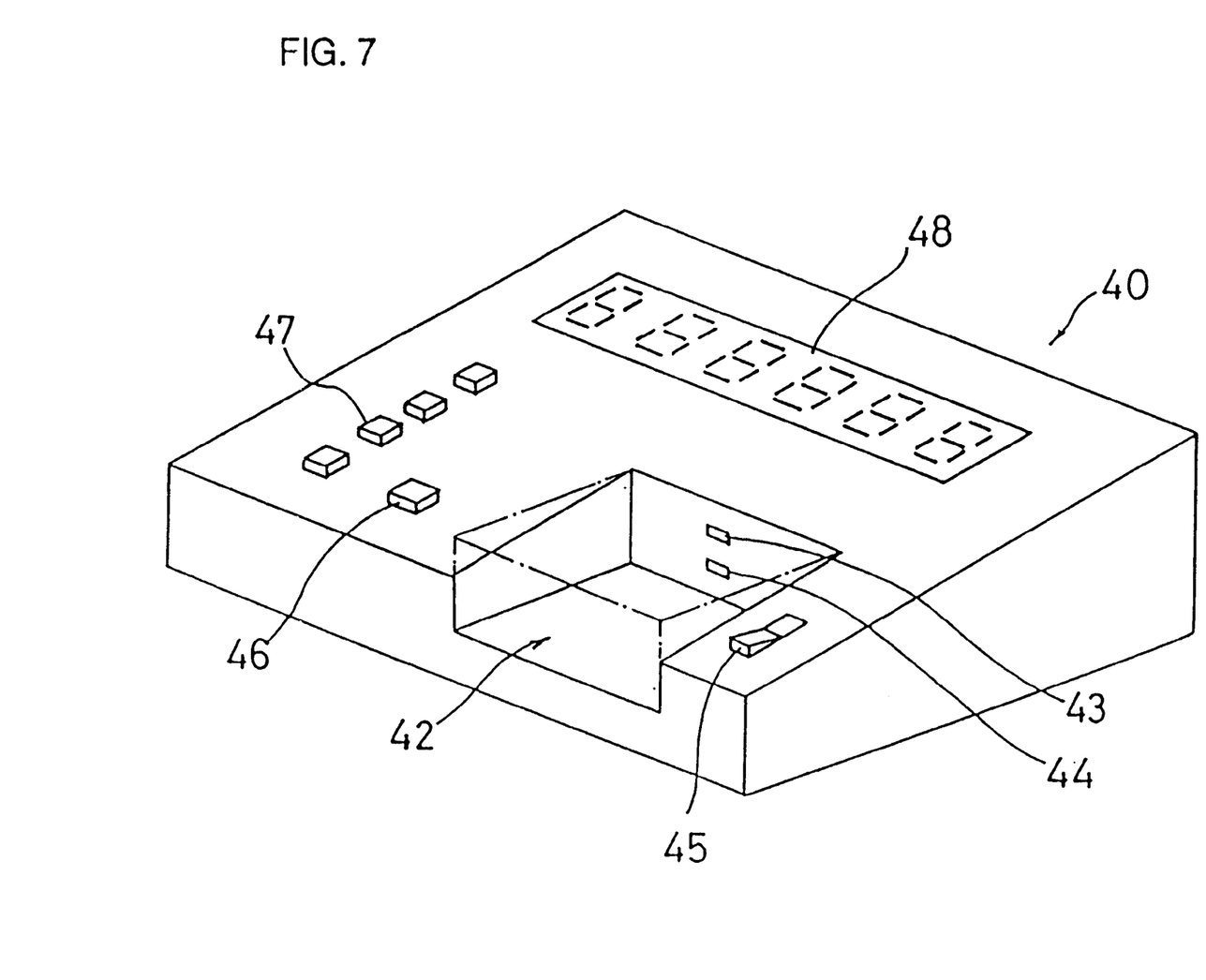
FIG. 7 is a drawing of the electroanalyzer in the present examples.

The constitution of the electroanalyzer of the present invention is described by reference to FIG. 7.

Coulometer 40 according to the present invention is provided with cutout part 42 equipped with terminals 43 and 44, electric power switch 45, start button 46, selection button 47 and indication part 48. When the galvanic cell 1 illustrated in Example 9 by reference to FIGS. 4–6 is attached as shown in the broken line, the electrode terminals 15 and 16 of the galvanic cell 1 come into contact respectively with the terminals 43 and 44 of the analyzer, and in this condition, the galvanic cell is ready for measurement. A coulometer (electrical quantity integrator) and a microprocessor are incorporated into the analyzer.

For analysis, the galvanic cell containing a specific electroactive substance is attached to the cutout part 42, then the substance to be measured is selected with the selection button 47, and the start button 46 is pushed, and the sample is injected into the galvanic cell. The role of the selection button 47 is to select a conversion formula of deriving the amount of the object substance from electric quantity integrated in the coulometer, and the role of the start button is to clear an internal memory (previously measured value).

According to the analyzer of the present invention, the galvanic cell 1 can be easily detached from the main body of analyzer 40, and a sample can be analyzed immediately (without any warm-up time) after the galvanic cell is attached to the analyzer 4 being connected to the electric source. Hence, a plural number of previously prepared galvanic cells can be used for the successive automatic multicomponent analysis in which a cell is exchanged for another cell successively in each measurement.

Example 11

Measurements were carried under the same conditions as in Example 2, using the galvanic cell including the lower felt 10 with a top surface of 7 cm$^3$, thickness of 5 mm, and volume of 3.5 cm$^3$ on the side of the working electrode and the upper felt 9 with a varying top surface of from 2 to 12 cm$^2$ and a varying volume of from 1 to 6 cm$^3$ on the side of the counter electrode. The results are shown in Table 5.

TABLE 5

| felt | A | B | C | D | E |
|---|---|---|---|---|---|
| top surface area of felt (cm$^2$) | 2 | 4 | 7 | 10 | 12 |
| felt thickness (mm) | 5 | 5 | 5 | 5 | 5 |
| volume (cm$^3$) | 1 | 2 | 3.5 | 5.0 | 6 |
| number of times of feasible measurements | 20 | 150 | 200 | 220 | — |
| background current ($\mu$A) | 2 | 7 | 8 | 8 | 15 |

In Table 5, the number of times of feasible measurements means the number of times 90% or more cell efficiency was obtained in successive measurements of 10 $\mu$l of 1×10$^{-4}$M NADH as a sample. The background current indicates a faint current flowing in the coulomb meter when the galvanic cell is attached thereto. This background current is caused e.g. by a capacitive current resulting from the electroactive substance in a cell. This causes noises in measurement, and interferes with accurate analysis. In a usual measurement, an S/N ratio within 1% is required for accuracy. To satisfy this requirement, the background current should be less than 10 $\mu A$ in this experiment.

As can be seen from the above results, each of the upper and lower felts preferably has a top surface area of $7\pm3$ cm$^2$ and a volume of $3.5\pm1.5$ ml. In the range outside the lower limits, the amount of sample injected is limited, and the number of times of successive measurements is also limited, and durability is deteriorated. On the other hand, the range outside the upper limits results in a rise in background current, thereby lowering the accuracy of measurement, which further results in poor dispersibility of a solution and high resistance leading to poor cell efficiency. A cell efficiency of 50% or less causes at least 1% S/N ratio, and is thus not preferable in respect of reproducibility and errors in measurement. An analytical device by a galvanic cell generally requires at least 50%, preferably at least 80%, cell efficiency. In the preferable range of the present example (i.e., the upper and lower felts each having a top surface area of $7\pm3$ cm$^3$ and a volume of $3.5\pm1.5$ ml), cell efficiency is preferably in the range of at least 80% for accurate measurements.

Example 12

NADH was measured under the same conditions as in Example 2, using the same galvanic cell as in Example 9 except that upper felt 9 (20 mm diameter) was provided on its periphery with a filter paper (Filter Paper No. 2 with an inner periphery diameter of 20 mm and an outer periphery diameter of 40 mm, manufactured by Advantech Co., Ltd.). As a result, the time required for each measurement could be reduced by use of filter paper, and good results could be stably obtained on 300 or more repeated measurements without exchanging the working electrode.

Various publications, including but not limited to certain Japanese Industrial Standards are cited herein, the disclosures of which are incorporated herein in their entirety by reference.

The entire disclosures of Japanese priority applications Nos. 290156/1992 filed Oct. 28, 1992, 30928/1993 filed Feb. 19, 1993, 163606/1993 filed Jul. 1, 1993, and 222527/1993 filed Sep. 9, 1993 are incorporated herein in their entirety by reference.

What is claimed is:

1. An apparatus for coulometric analysis for the quantitative determination of a substance in a sample comprising:
   a first electrode containing at least a mediator, wherein said mediator is capable of reacting with said substance to produce a first electroactive species;
   a second electrode containing a second electroactive species, wherein said first electroactive species and said second electroactive species have an electrochemical potential difference;
   an ion-permeable membrane situated between said first and said second electrodes; and
   means for measuring an electrical quantity generated by said electrochemical potential difference without application of an external power source, whereby said electrical quantity is used to quantify said substance.

2. The apparatus according to claim 1, wherein said first electroactive species oxidizes at a first electrochemical potential, said second electroactive species reduces at a second electrochemical potential, and wherein said first electrochemical potential is lower than said second electrochemical potential.

3. The apparatus according to claim 1, wherein said first electroactive species undergoes oxidation at a low potential and said second electroactive species is reduced at a high potential.

4. The apparatus according to claim 1, wherein the first electrode undergoes oxidation at a high potential and the second substance is reduced at a low potential.

5. A coulometric analyzer for use in combination with the apparatus according to claim 1 comprising:
   (a) a cutout part to receive the apparatus;
   (b) a pair of terminals exposed on said cutout part capable of coming into contact respectively with a pair of electrode terminals of said apparatus;
   (c) a current integration means being connected to both of the terminals of part (b);
   (d) an indication part;
   (e) an analysis item selection part;
   (f) a start button allowing said electric current integration means to initiate current integration; and
   (g) an arithmetical means for converting the resulting integrated current quantity into an amount of sample substance and communicating with said indication part to indicate the amount of sample substance.

6. The apparatus according to claim 1, wherein said first electrode also contains an electrolyte selected from the group consisting of a phosphate buffer, hydrochloric acid, sulfuric acid, potassium chloride, and solutions thereof.

7. The apparatus according to claim 1, wherein the mediator is selected from the group consisting of 5-methylphenazinium methyl sulfate, 1-methoxy-5-methylphenazinium methyl sulfate, 9-dimethylaminobenzo ($\alpha$) phenoxadine-7-ium chloride, 3,7-bis(dimethylamino) phenothiazine-5-ium chloride, hexacyanoferrate (III) ion, Vitamin K$_3$, meldola blue and salts thereof.

8. The apparatus according to claim 1, wherein said second electroactive species is selected from the group consisting of hexacyanoferrate (III) ion, hexacyanoferrate (II) ion, and permanganate ion, and salts thereof.

9. The apparatus according to claim 8, wherein the substance is glutamic acid, and the mediator is glutamate dehydrogenase, and wherein glutamic acid reacts with glutamate dehydrogenase to produce the first electroactive species, which is NADH.

10. The apparatus according to claim 8, wherein the substance is ascorbic acid.

11. An apparatus for coulometric analysis for the quantitative determination of a substance in a sample comprising:
    a first electrode containing at least a mediator, wherein said mediator is capable of reacting with said substance to produce a first electroactive species;
    a second electrode containing a second electroactive species;
    an ion-permeable membrane situated between said first and said second electrodes; and
    means for measuring an electrical quantity generated by at least one self-driven reaction between said first electroactive species and said second electroactive species, whereby said electrical quantity is used to quantify said substance.

12. The apparatus according to claim 11, wherein said first electroactive species oxidizes at a first electrochemical potential, said second electroactive species reduces at a second electrochemical potential and wherein said first electrochemical potential is lower than said second electrochemical potential.

13. The apparatus according to claim 11, wherein said first electroactive species undergoes oxidation at a low potential and said second electroactive species is reduced at a high potential.

14. The apparatus according to claim 11, wherein the first electrode undergoes oxidation at a high potential and the second substance is reduced at a low potential.

15. A coulometric analyzer for use in combination with the apparatus according to claim 11 comprising:
(a) a cutout part to receive the apparatus;
(b) a pair of terminals exposed on said cutout part capable of coming into contact respectively with a pair of electrode terminals of said apparatus;
(c) a current integration means being connected to both of the terminals of part (b);
(d) an indication part;
(e) an analysis item selection part;
(f) a start button allowing said electric current integration means to initiate current integration; and
(g) an arithmetical means for converting the resulting integrated current quantity into an amount of sample substance and communicating with said indication part to indicate the amount of sample substance.

16. The apparatus according to claim 11, wherein said first electrode also contains an electrolyte selected from the group consisting of a phosphate buffer, hydrochloric acid, sulfuric acid, potassium chloride, and solutions thereof.

17. The apparatus according to claim 11, wherein said mediator is selected from the group consisting of 5-methylphenazinium methyl sulfate, 1-methoxy-5-methyl-phenazinium methyl sulfate, 9-dimethylaminobenzo (α) phenoxadine-7-ium chloride, 3,7-bis(dimethylamino) phenothiazine-5-ium chloride, hexacyanoferrate (III) ion, Vitamin $K_3$ meldola blue and salts thereof.

18. The apparatus according to claim 11, wherein said second electroactive species is selected from the group consisting of hexacyanoferrate (III) ion, hexacyanoferrate (II) ion, and permanganate ion, and salts thereof.

19. An apparatus for coulometric analysis for the quantitative determination of an aqueous substance in a sample comprising:
a first electrode having a hydrophilic and conductive material that is impregnated with at least a mediator, wherein said mediator is capable of reacting with said sample to produce a first electroactive species;
a second electrode having a hydrophilic and conductive material that is impregnated with a second electroactive species, wherein said first electroactive species and said second electroactive species have an electrochemical potential difference;
an ion-permeable membrane situated between said first and said second electrodes; and
means for measuring an electrical quantity generated by said electrochemical potential difference without application of an external power source, whereby said electrical quantity is used to quantify said substance.

20. The apparatus according to claim 19, wherein the mediator is selected from the group consisting of 5-methylphenadinium methyl sulfate, 1-methoxy-5-methyl-phenazinium methyl sulfate, 9-dimethylaminobenzo (α) phenoxadine-7-ium chloride, 3,7-bis(dimethylamino) phenothiazine-5-ium chloride, hexacyanoferrate (III), Vitamin $K_3$, meldola blue and salts thereof.

21. The apparatus according to 20, wherein said second electroactive species is selected from the group consisting of hexacyanoferrate (III) ion, hexacyanoferrate (II), permanganate ion, and salts thereof.

22. The apparatus according to claim 19, wherein said first electroactive species oxidizes at a first electrochemical potential, said second electroactive species reduces at a second electrochemical potential and wherein said first electrochemical potential is lower than said second electrochemical potential.

23. An apparatus for coulometric analysis for the quantitative determination of an aqueous non-electroactive substance in a sample comprising:
a first electrode containing a first aqueous solution including at least the sample and a mediator, wherein said mediator is capable of reacting with said non-electroactive sample to produce a first electroactive species;
a second electrode containing a second electroactive species;
an ion-permeable membrane situated between said first and said second electrodes; and
means for measuring an electrical quantity generated by a potential difference between said first and said second electroactive species without application of an external power source, whereby said electrical quantity is used to quantify said substance.

24. The apparatus according to claim 23, wherein said first electrode comprises a hydrophilic and conductive material impregnated with said mediator; and
said second electrode comprises a hydrophilic and conductive material impregnated with said second electroactive species.

25. The apparatus according to claim 24, wherein said hydrophilic and conductive material of said first electrode directly contacts a first side of said ion-permeable membrane; and
said hydrophilic and conductive material of said second electrode directly contacts a second side of said ion-permeable membrane.

26. The apparatus according to claim 24, wherein the hydrophilic and conductive material of said first electrode is selected from the group consisting of carbon and conductive metals; and
said hydrophilic and conductive material of said second electrode is selected from the group consisting of carbon and conductive metals.

27. The apparatus according to claim 23, wherein the mediator is selected from the group consisting of 5-methylphenadinium methyl sulfate, 1-methoxy-5-methyl-phenazinium methyl sulfate, 9-dimethylaminobenzo (α) phenoxadine-7-ium chloride, 3,7-bis(dimethylamino) phenothiazine-5-ium chloride, hexacyanoferrate (III), Vitamin $K_3$ meldola blue and salts thereof.

28. The apparatus according to claim 23, wherein said second electroactive species is selected from the group consisting of hexacyanoferrate (III) ion, hexacyanoferrate (II) ion, permanganate ion and salts thereof.

* * * * *